United States Patent [19]

Tradowsky

[11] 4,365,955
[45] Dec. 28, 1982

[54] DENTAL ARTICULATOR

[76] Inventor: Michael Tradowsky, 10370 Blair La., Kirtland, Ohio 44094

[21] Appl. No.: 260,406

[22] Filed: May 4, 1981

[51] Int. Cl.³ .............................................. A61C 11/00
[52] U.S. Cl. ........................................ 433/57; 433/54; 434/264
[58] Field of Search ..................................... 433/54–67

[56] References Cited

U.S. PATENT DOCUMENTS

| | | | |
|---|---|---|---|
| 1,586,739 | 6/1926 | Hanau | 433/62 |
| 2,119,896 | 6/1938 | Van Dorn et al. | 433/59 |
| 3,048,923 | 8/1962 | Franwick | 433/55 |
| 3,159,915 | 12/1964 | Beu et al. | 433/57 |
| 3,330,039 | 7/1967 | Brandhandler et al. | 433/67 |
| 3,616,537 | 11/1971 | Shuchard | 434/264 |
| 3,624,906 | 12/1971 | Granger | 433/57 |
| 3,897,632 | 8/1975 | Beu | 433/56 |
| 4,305,708 | 12/1981 | Beu | 433/57 |

Primary Examiner—Gene Mancene
Assistant Examiner—John J. Wilson
Attorney, Agent, or Firm—Maky, Renner, Otto & Boisselle

[57] ABSTRACT

A dental articulator in which maxillary and mandibular frames have at opposite sides interengaged condylar elements to simulate the jaw movements of a dental patient whose maxillary and mandibular dental casts are mounted on the respective frames. The mandibular frame has condylar spheres slidably engaged between upper and lower parallel side walls of grooves in condylar guide elements angularly adjustable on opposite sides of the maxillary frame, the upper side walls of the grooves being transparent for visual observation of the orbital and rotational movements of the condylar spheres in the grooves during relative movements of the frames to simulate the jaw movements of the dental patient. The bottom walls of the grooves in the condylar guide elements are spaced axially inwardly of the surfaces of the respective spheres to determine the maximum side shift of the maxillary frame with respect to the mandibular frame and adjusting screws extending through the respective spheres are adjustable toward and away from the bottom walls of the respective grooves to adjust the side shift to a desired value between zero and maximum. The lower side wall of each groove has therein a rotatably adjustable chordwise disposed cam to engage the respective spheres to determine the lateral shift of the rotating condylar sphere. The dental articulator is further characterized in the provision of a simple bracket pivotally mounted on the maxillary frame and including a single screw engaged with the maxillary frame to lock the frames for centric jaw opening and closing movements about a hinge axis coinciding with the axis of the condylar spheres.

7 Claims, 7 Drawing Figures

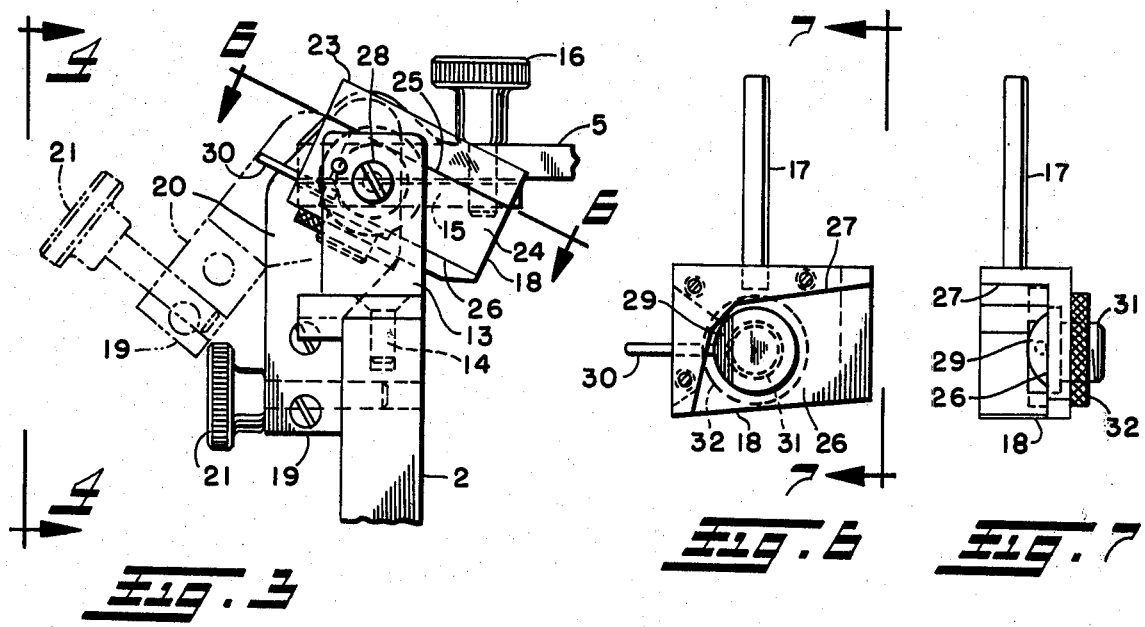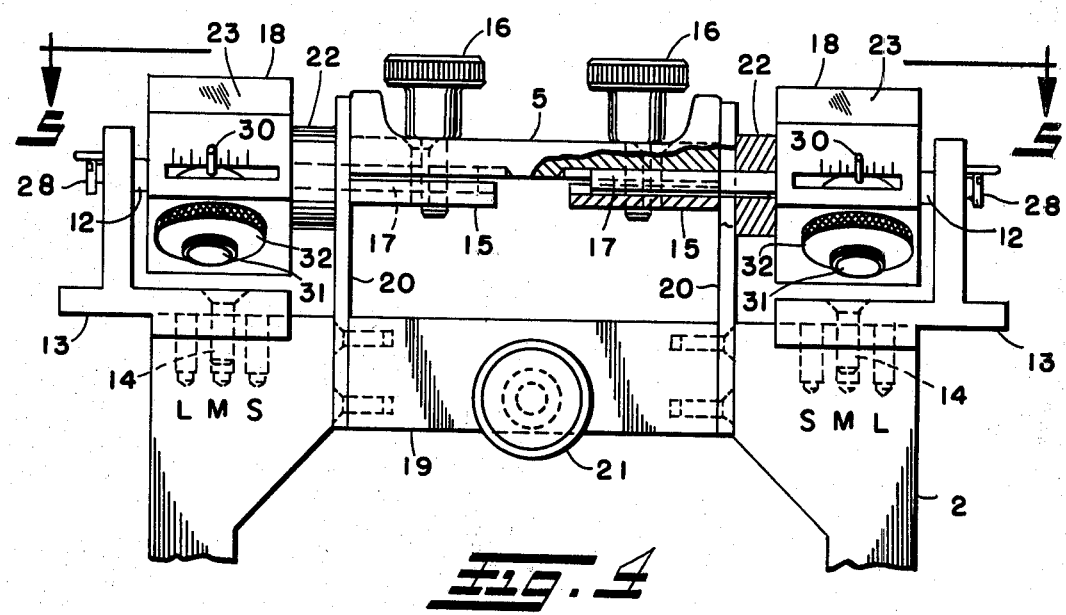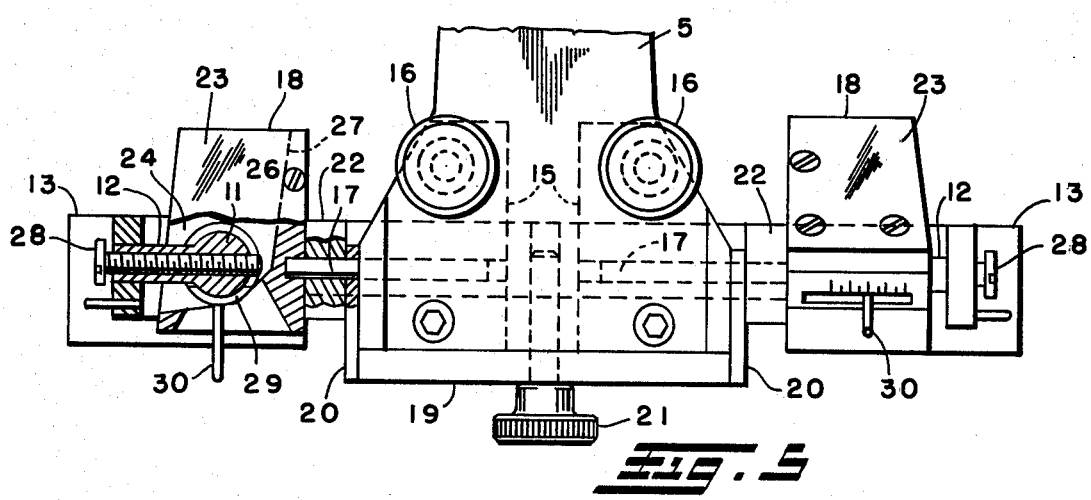

DENTAL ARTICULATOR

BACKGROUND OF THE INVENTION

Dental articulators are used to teach jaw movements in dental schools and to fabricate dentures and fixed bridgework in dental laboratories, the parts of the articulator that simulate the jaw joints being commonly referred to as condylar elements which generally consist of spheres that move in adjustable tracks or along adjustable cams. In known articulators movements of the condylar spheres are obscured by metal plates, cam mechanisms and the like whereby the teaching of condylar movements cannot be seen nor can it be verified that the articulator is moving correctly during fabrication of dental restorations.

Moreover, in known articulators the bodily side shift of the condylar spheres is adjusted by a cam which is moved toward and away from either the orbiting condylar sphere or the rotating condylar sphere to respectively decrease or increase the bodily side shift.

In some known articulators the condylar spheres move in milled tracks and therefore the mobility of the spheres is limited by the mobility of the tracks and in other instances the spheres are engaged only by the upper wall of a condylar guide element which permits separation of the spheres from the upper walls during fabrication of dental work which can lead to faults therein.

Another characteristic of known articulators is that centric locks are provided by screws which block the respective condylar spheres in their respective tracks or in some instances spring loaded cam mechanisms are provided for holding the maxillary and mandibular frames in centric relation for pivotal opening and closing movement about a hinge axis while preventing or resisting left and right lateral excursions or protrusive excursions of the jaw.

SUMMARY OF THE INVENTION

In contradistinction to known articulators the condylar spheres are slidable between upper and lower parallel side walls of grooves in condylar guide elements for orbital and rotational movements, such movements being at all times visible through clear transparent upper side walls of the guide elements. The condylar spheres have a clearance with the bottoms of the grooves in the condylar guide elements which determine the maximum side shift of the maxillary frame with respect to the mandibular frame during the initial portion of the lateral excursion movement of the maxillary frame with respect to the mandibular frame. Adjustment of the bodily side shift is provided by an adjusting screw in each condylar sphere which is adjustable toward or away from the respective bottom wall of the groove in the condylar guide element to vary the bodily side shift between zero and maximum.

In further contradistinction to known articulators the present articulator provides a cam adjustment for the lateral shift on the rotating side disposed beneath the condylar sphere and rotatably adjustable to laterally shift the condylar sphere to the desired extent without interfering with unobstructed visual observation of the condylar sphere movements through the transparent upper wall of the condylar guide element groove.

It is a further object of this invention to provide a simplified centric lock mechanism which is detachably engaged with the mandibular frame by a single screw to restrict opening and closing movement of the maxillary frame about a fixed hinged axis coinciding with the axis of the condylar spheres.

BRIEF DESCRIPTION OF THE DRAWING

In the annexed drawing:

FIG. 3 is a fragmentary side elevation view as viewed from the left side of FIG. 1, the phantom line showing the centric lock in unlocked position for lateral excursions of the maxillary frame for orbital and rotational movement of the condylar spheres in the condylar guide elements;

FIG. 4 is a fragmentary rear elevation view as viewed along line 4—4 from the lefthand side of FIG. 3, one of the condylar guide element angular adjustment clamps being shown in cross section;

FIG. 5 is a top plan view as viewed along line 5—5 from the top of FIG. 4;

FIG. 6 is a top plan view of a condylar guide element alone along line 6—6, FIG. 3, showing the adjustable cam to control the lateral shift of the rotating condylar sphere; and FIG. 7 is an elevation view as viewed along line 7—7 from the righthand side of FIG. 6.

DETAILED DESCRIPTION OF A PREFERRED EMBODIMENT

Figure 1:
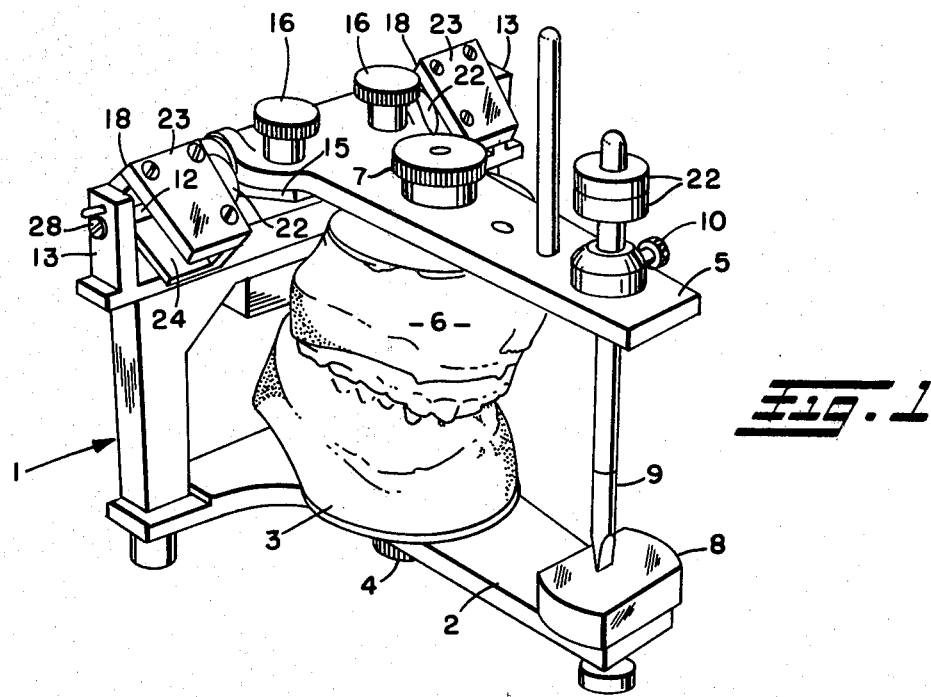
FIG. 1 is a perspective view of a dental articulator embodying the present invention.

The dental articulator 1 herein shown comprises a mandibular frame 2 on which a lower dental cast 3 is mounted by a thumbscrew 4, the cast 3 bearing the same location to the hinge axis of the articulator 1 as the dental patient's jaw bears to the temporomandibular (jaw) joints of the patient in the centric position of the mandible. As well known in the art, the jaw hinge axis in the centric position of the mandible may be determined by a jaw hinge axis locater such as a hinge bow or a face bow. In the centric position of the articulator 1 the maxillary frame 5 is at its rear end hinged about a hinge axis and an upper dental cast 6 is mounted on the maxillary frame 5 by the thumbscrew 7 for opening and closing of the casts 3 and 6 about such hinge axis. The mandibular frame 2 has at its front end a rest block 8 which is engaged by an incisal pin 9 which is vertically adjustably mounted at the front end of the maxillary frame 5 to allow the dental casts 3 and 6 to come together or to be spaced apart as desired. The incisal pin 9 is locked in adjusted position by thumbscrew 10.

The upper rear portion of the mandibular frame 2 has opposite condylar spheres 11 with coaxial horizontal stem or shaft portions 12 fixed in vertical legs of mounting brackets 13. The brackets 13 are mounted on the mandibular frame 2 by screws 14 at one of the L M S positions to space the condylar spheres 11 a distance corresponding to the spacing of the condyles of a dental patient according to whether the patient has a large, medium or small jaw.

The rear end of the maxillary frame 5 has on opposite sides thereof coaxial clamps 15 actuated by thumbscrews 16 to clamp the shafts 17 of condylar guide elements 18 for angular adjustment of the latter about the axis of said shafts 17. A centric lock bracket 19 has arms 20 on opposite sides of the maxillary frame 5 pivotally mounted on the shafts 17 of the condylar guide elements 18 and when the bracket 19 is secured by the screw 21 to the mandibular frame 2, shafts 17 are held by arms 20 in coaxial relation to spheres 11 so that the maxillary frame 5 is constrained for pivotal movement about the common axis of the condylar spheres 11 and guide element shafts 17, thus establishing the centric relation of the dental casts 3 and 6 with opening and closing movements about such fixed hinge axis.

When the condylar sphere bracket 13 is mounted in the M position as shown, a spacer 22 will be mounted on each shaft 17 as shown. When the sphere brackets 13 are in the S position, the spacers 22 are omitted and the shafts 17 are inserted further into the clamps 15 until the inner sides of the guide elements 18 engage the arms 20 of the centric lock bracket 19. On the other hand, when the sphere brackets 13 are in the L position two of such spacers 22 will be employed on each shaft 17. For convenience, the unused spacers 22 may be stored on the upper end of the incisal pin 9.

Each condylar guide element 18 has an upper clear transparent plate 23. Each condylar guide element 18 (with the transparent plate 23 attached) defines a radially extending groove 24 having parallel upper and lower walls 25 and 26 with which the associated condylar sphere 11 has sliding engagement. In the centric position of the articulator 1 the bottom wall 27 of each groove 24 is spaced from the associated condylar sphere 11 to determine the maximum bodily side shift (e.g. 2 mm.) of the maxillary frame 5 upon release of the centric lock 19. In order to vary the side shift to correspond to the side shift as determined by left and right lateral excursion check bites of the dental patient, an adjusting screw 28 extending through each stem portion 12 and sphere 11 may be adjusted so that its axially inner end establishes a predetermined clearance with wall 27 for adjusting the side shift. Preferably, when the adjusting screws 28 are turned all the way inward, the inner ends thereof will engage the respective bottom walls 27 so that there will be no bodily side shift and from this position the screws 28 may be unscrewed predetermined angles to obtain predetermined clearances which determine the bodily side shift in both directions.

Protrusive, left lateral, and right lateral excursions of the patient's mandible may advantageously be taken by a vise as disclosed in my U.S. Pat. No. 4,026,024 granted May 31, 1977 and entitled "Vise for Transfer of Check-Bites". There are of course other known devices for establishing the check bites for transfer to the dental articulator 1 for adjusting the articulator 1 to duplicate the movements of the jaw joints during protrusive and lateral excursions of the patient's mandible.

When the centric lock 19 has been released (after adjustment of the articulator 1 to correspond with the patient's check bites), the dental casts 3 and 6 can be relatively moved to correspond to the excursions of the patient's mandible to note any malocclusions and to enable fabrication of correct dentures or bridgework.

For example, if the maxillary frame 5 is actuated to the left as viewed in FIG. 1 corresponding to a left lateral excursion of the patient's jaw, the maxillary frame 5 will shift bodily sideward until the bottom wall 27 of the groove 24 engages the end of the left adjusting screw 28 (or engages the left condylar sphere 11 if the screw 28 is adjusted for maximum bodily side shift). The left condylar sphere 11 then becomes the orbiting condyle which orbits in a path as determined by the angle of the upper and lower walls 25 and 26 of the left condylar guide element 18 and by the bottom wall 27 of the groove 24 of the left condylar guide element 18. In this case, the right condylar sphere 11 constitutes the working or rotating condyle and if the check bite has shown a lateral shift, the rotatably adjustable chordwise cam 29 underneath the condylar sphere 11 effects such lateral shift of the condylar sphere 11 on the working or rotating side while the other side is the orbiting or balancing side. On different patients the lateral shift may be rearward or forward and hence the cam 29 is adjustable by pin 30 either way from the straight lateral shift position shown in FIG. 6. The cam 29 has a flat upper surface which is flush with the lower wall 26. The threaded shank 31 of the cam 29 extends through a hole in the guide element 18 and has a locknut 32 for locking the cam 29 in desired adjusted position.

When the maxillary frame is shifted to the right as shown in FIG. 1 corresponding to a right lateral excursion of the patient's mandible, the left condylar sphere 11 becomes the working or rotating side and the right condylar sphere 11 becomes the orbiting or balancing side entailing a bodily side shift of the maxillary frame 5 toward the right to take up the clearance between the bottom wall 27 of the right condylar guide element 18 and the right adjusting screw 28 for following the angular path of walls 25 and 26 and the path of the bottom wall 27. It has been found that the angle of the bottom wall 27 should be $7\frac{1}{2}°$.

Figure 2:
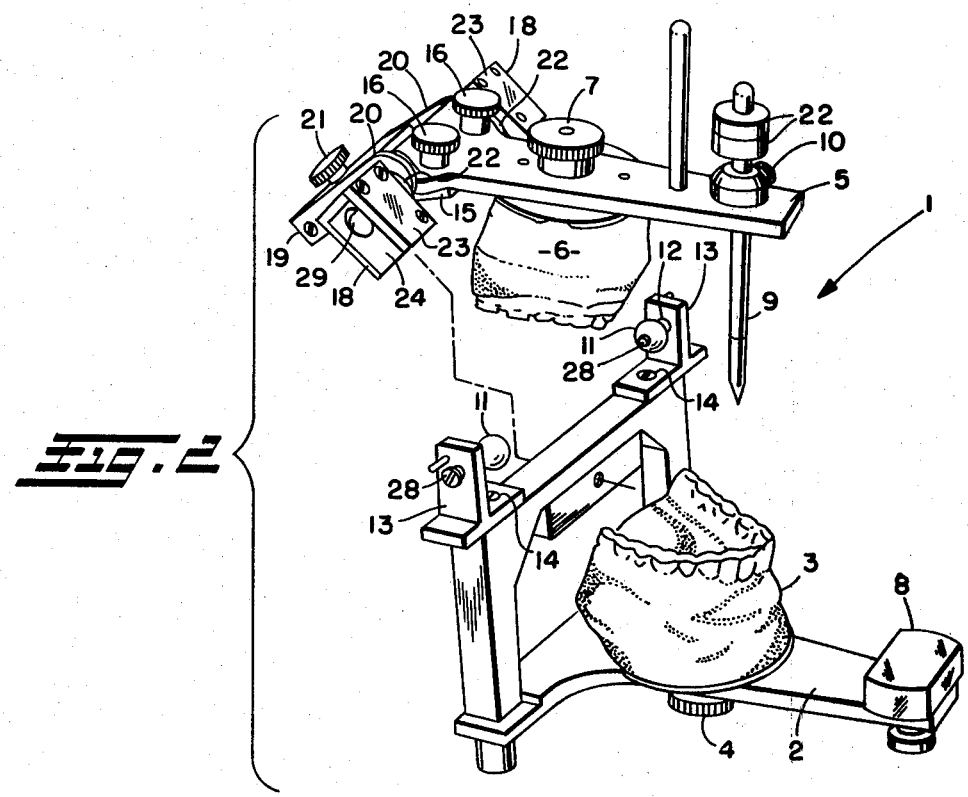
FIG. 2 is a perspective view showing the mandibular and maxillary frames in separated condition.

As can be seen, the dental articulator 1 herein duplicates the jaw movements of individual dental patients. Articulators are generally used in dental schools to teach jaw movements and in dental laboratories to fabricate dentures and fixed bridgework. In view of the transparent upper plates 23 of the condylar guide elements 18, the movements of the condylar spheres 11 are clearly visible to facilitate the teaching of condylar movements. The visual observation also enables verification that the articulator 1 is moved correctly during the fabrication of dental restorations. The condylar guide elements 18 with grooves 24 as described enables ready separation of the maxillary and mandibular frames 5 and 2 as shown in FIG. 2 and because the condylar spheres 11 move between parallel walls 25 and 26 of the grooves 24 there is no possibility of separation of the upper walls 25 from the condylar spheres 11 as is possible in some prior art articulators.

Moreover, the lateral shift cams 29 are disposed chordwise beneath the condylar spheres 11 so that the condylar spheres 11 remain free for observation of condylar movements through the transparent plates 23 of the condylar guide elements 18.

The embodiments of the invention in which an exclusive property or privilege is claimed are defined as follows:

1. A dental articulator comprising mandibular and maxillary frames adapted to mount a dental patient's respective lower and upper dental casts, said frames having interengaged condylar elements on opposite sides thereof corresponding to the patient's temporomandibular joints for movement of said maxillary frame relative to said mandibular frame to positions corresponding to the check bites of lateral excursions of the patient's jaw; said condylar elements comprising horizontally spaced apart condylar spheres having axially outwardly extending coaxial horizontal stem portions fixed to said mandibular frame, and condylar guide elements angularly adjustably secured on opposite sides of said maxillary frame; said guide elements having axially and radially outwardly open radially extending grooves including parallel upper and lower walls slidably embracing the respective spheres to define, upon movement of said maxillary frame to the aforesaid positions, a pivot for the rotating sphere and a condylar path for the orbiting sphere, each groove having a bottom wall which, in centric position of said maxillary frame, is axially spaced from the associated sphere to establish a maximum bodily side shift of said maxillary frame when moved to the aforesaid positions; and an axially inwardly extending adjusting screw in threaded engagement with and extending through each stem portion and sphere; each screw having an axially outer end accessible for turning of said screw and having an axially inner end movable toward or away from the associated bottom wall responsive to turning of said screw thereby to adjust the bodily side shift to a predetermined value between zero and maximum.

2. The articulator of claim 1 wherein said upper walls are transparent for visual observation of said spheres and their rotating, orbiting, side shift movements in said grooves.

3. The articulator of claim 1 wherein each condylar guide element has an axially inwardly extending shaft portion; and wherein said maxillary frame has clamp means to clamp said shaft portions in coaxial relation and in predetermined angularly adjusted positions of said grooves.

4. The articulator of claim 3 wherein a centric lock member releasably secured to said mandibular frame has arms which retain said maxillary frame in centric position against bodily side shift and to which the respective shaft portions are pivotally connected about an axis coinciding with the axis of said stem portions and spheres to define a hinge axis about which said maxillary frame is swingable to correspond to the patient's centric jaw opening and closing movements.

5. The articulator of claim 4 wherein a single screw carried by said lock member has threaded engagement with a threaded hole in said mandibular frame to releasably secure said lock member to said mandibular frame.

6. The Articulator of claim 1 wherein each lower wall has therein a chordwise disposed cam rotatably adjustable about an axis perpendicular to said lower wall for engagement with the rotating condylar sphere to determine the magnitude and direction of lateral shift of the rotating sphere responsive to bodily side shift of said maxillary frame.

7. The articulator of claim 6 wherein said upper walls are transparent for visual observation of said spheres and their rotating, orbiting, side shift, lateral shift movements in said grooves.

* * * * *